(12) United States Patent
Gerlett

(10) Patent No.: US 11,931,554 B2
(45) Date of Patent: Mar. 19, 2024

(54) SYSTEMS, KITS AND METHODS FOR LOADING AND DELIVERING A SMALL VOLUME DOSE FROM A SYRINGE

(71) Applicant: ICON BIOSCIENCE, INC., Watertown, MA (US)

(72) Inventor: Cathy Ann Gerlett, Klamath Falls, OR (US)

(73) Assignee: ICON BIOSCIENCE, INC., Watertown, MA (US)

( * ) Notice: Subject to any disclaimer, the term of this patent is extended or adjusted under 35 U.S.C. 154(b) by 339 days.

(21) Appl. No.: 17/408,908

(22) Filed: Aug. 23, 2021

(65) Prior Publication Data

US 2021/0379291 A1    Dec. 9, 2021

Related U.S. Application Data

(63) Continuation of application No. 16/269,910, filed on Feb. 7, 2019, now Pat. No. 11,097,061.

(60) Provisional application No. 62/628,446, filed on Feb. 9, 2018.

(51) Int. Cl.
*A61M 5/315* (2006.01)
*A61M 5/28* (2006.01)

(52) U.S. Cl.
CPC .......... *A61M 5/31541* (2013.01); *A61M 5/28* (2013.01); *A61M 5/31525* (2013.01); *A61M 5/31573* (2013.01); *A61M 5/31578* (2013.01); *A61M 5/3159* (2013.01)

(58) Field of Classification Search
CPC ...... A61M 2005/3142; A61M 5/31525; A61M 5/3153; A61M 5/31563
See application file for complete search history.

(56) References Cited

U.S. PATENT DOCUMENTS

| | | | |
|---|---|---|---|
| 3,770,026 A | 11/1973 | Isenberg | |
| 4,246,898 A | 1/1981 | Travelent et al. | |
| 4,874,385 A | 10/1989 | Moran et al. | |
| 5,833,669 A | 11/1998 | Wyrick | |
| 5,975,355 A | 11/1999 | Cecala et al. | |
| 10,022,502 B2 | 7/2018 | Wong et al. | |
| 10,258,502 B2 | 4/2019 | Tsai et al. | |
| 2003/0225358 A1 | 12/2003 | Berman et al. | |

(Continued)

FOREIGN PATENT DOCUMENTS

| | | |
|---|---|---|
| CN | 101039709 A | 9/2007 |
| CN | 107223042 A | 9/2017 |

(Continued)

OTHER PUBLICATIONS

Chinese Office Action dated Jan. 12, 2022 issued in corresponding Chinese Patent Application No. 201980012234.9.

(Continued)

*Primary Examiner* — Deanna K Hall
(74) *Attorney, Agent, or Firm* — MEDLER FERRO WOODHOUSE & MILLS PLLC

(57) ABSTRACT

A kit is disclosed for accurately loading a small volume dose of a medication within a syringe and for delivering the small volume dose of the medication at a treatment site. The kit generally includes a loading and delivery system in accordance herewith, a syringe, and a medication. The loading and delivery system includes a syringe delivery ring and a syringe loading guide, which may be used for example, to administer a small volume dose of a medication at the end of an ocular surgery.

14 Claims, 20 Drawing Sheets

(56) References Cited

U.S. PATENT DOCUMENTS

| | | |
|---|---|---|
| 2005/0008683 A1 | 1/2005 | Mikszta et al. |
| 2008/0221517 A1 | 9/2008 | Shaw et al. |
| 2011/0190709 A1 | 8/2011 | Mitsuno et al. |
| 2014/0180245 A1 | 6/2014 | Wong et al. |
| 2016/0120879 A1 | 5/2016 | Wong et al. |
| 2019/0247585 A1 | 8/2019 | Gerlett |

FOREIGN PATENT DOCUMENTS

| | | |
|---|---|---|
| DE | 3410336 A1 | 5/1985 |
| DE | 3509865 A1 | 9/1986 |
| DE | 202009011284 U1 | 3/2010 |
| EP | 1559443 A1 | 8/2005 |
| EP | 1702636 A1 | 9/2006 |
| EP | 2701778 | 3/2014 |
| JP | 2004500201 A | 1/2004 |
| JP | 2009018196 A | 1/2009 |
| JP | 2014516087 A | 7/2014 |
| WO | 2007042592 A1 | 4/2007 |
| WO | 2009095735 A1 | 8/2009 |
| WO | 2012/148717 A1 | 11/2012 |
| WO | 2012149040 A2 | 11/2012 |
| WO | 2014190248 A1 | 11/2014 |

OTHER PUBLICATIONS

EESR issued on Sep. 29, 2021 in corresponding EP application No. 19750910.2.

Uppal N., et al., Drug Formulations that Require Less than 0.1 ml of Stock Solution to Prepare Doses for Infants and Chiidren, CMAJ 183(4): E246-E248 (Research Letter), Mar. 8, 2011, E246 Abstract.

International Search Report and Written Opinion of International Application No. PCT/US2019/017081, dated Apr. 23, 2019.

Office Action dated Dec. 23, 2022 in Japanese Patent Appl. No. 2020-540784 (with English language translation).

Search Report dated Dec. 1, 2022 in Japanese Patent Appl. No. 2020-540784.

SYSTEMS, KITS AND METHODS FOR LOADING AND DELIVERING A SMALL VOLUME DOSE FROM A SYRINGE

CROSS-REFERENCE TO RELATED APPLICATION

The present application is a continuation of prior U.S. application Ser. No. 16/269,910, filed Feb. 7, 2019, now U.S. Pat. No. 11,097,061, issued Aug. 24, 2021, which claims the benefit of prior filed U.S. Appl. No. 62/628,446, filed Feb. 9, 2018, each of which is incorporated by reference herein in its entirety.

FIELD OF THE INVENTION

The present technology relates to dose guides for injection syringes. More specifically, the present invention relates to systems, kits and methods for accurately loading and delivering a small volume dose of a medication with a syringe.

BACKGROUND OF THE INVENTION

Medications are often delivered to a patient with a syringe. For patient safety, it is imperative that the proper volume or dose of the medication is delivered by the syringe. This is particularly important for medications delivered in small volumes, where even a minimal variation in the delivered volume can have adverse effects.

Further, medications are often delivered by the patient, or a caregiver who may have difficulty in handling and operating the syringe during the loading and delivery process. Even when operated by a skilled user, loading and delivery of small volumes with a syringe may be challenging. For example, current loading systems provide insufficient stability to accurately load a desired small volume dose, such as a dose of less than 10 μl, of a medication into a syringe. Further, syringes often have a deformable plunger seal. When a user exerts pressure on a plunger to deliver a medication, the plunger seal can deform when contacting a distal end of the syringe barrel. The deformed plunger seal may lead to a larger than intended volume of the medication being delivered.

Accordingly, there is a need for a simple, yet accurate and stable means for loading and delivering medication via an injection syringe that provides a more accurate small volume dose delivery using existing syringes.

BRIEF SUMMARY OF THE INVENTION

Embodiments hereof are directed to a kit for accurately loading a small volume dose of a medication within a syringe and for delivering the small volume dose of the medication at a treatment site. The kit includes a syringe, a syringe delivery ring, a syringe loading guide and a medication. In an embodiment the medication may be in a vial or pre-loaded within the syringe. The syringe delivery ring includes a lumen and a sidewall opening that extend from a proximal end to a distal end thereof, the sidewall opening being configured to permit a plunger rod of the syringe to traverse the sidewall opening and to be slidably received within the lumen of the syringe delivery ring to thereby couple the syringe delivery ring to the plunger rod. The syringe delivery ring further includes a proximal segment and a distal segment with a proximal-facing bearing surface, wherein an outer diameter of the proximal segment is smaller than an outer diameter of the distal segment. The syringe loading guide includes a proximal-facing surface for abutting with a plunger flange of the syringe during loading, a distal-facing surface for abutting with the bearing surface of the distal segment of the syringe delivery ring during loading, and a coupling archway that is configured to attach to the proximal segment of the syringe delivery ring during loading. A first height of the syringe loading guide is greater than a second height of the proximal segment of the syringe delivery ring, wherein a difference between the first height of the syringe loading guide and the second height of the proximal segment of the syringe delivery ring corresponds to a distance a plunger seal of the syringe travels within a barrel of the syringe to deliver a small volume dose of the medication.

Embodiments hereof are directed to a loading and delivery system for use with a syringe to accurately load a small volume dose of a medication within the syringe and to deliver the small volume dose from the syringe at a treatment site. The system includes a syringe delivery ring and a syringe loading guide. The syringe delivery ring includes a lumen and a sidewall opening that extend from a proximal end to a distal end thereof, the sidewall opening being configured to permit a plunger rod of a syringe to traverse the sidewall opening and to be slidably received within the lumen of the syringe delivery ring to thereby couple the syringe delivery ring to the plunger rod. The syringe delivery ring further includes a proximal segment and a distal segment with a proximal-facing bearing surface, wherein an outer diameter of the proximal segment is smaller than an outer diameter of the distal segment. The syringe loading guide includes a proximal-facing surface for abutting with a plunger flange of the syringe during loading, a distal-facing surface for abutting with the bearing surface of the distal segment of the syringe delivery ring during loading, and a coupling archway that is configured to attach to the proximal segment of the syringe delivery ring during loading. A first height of the syringe loading guide is greater than a second height of the proximal segment of the syringe delivery ring.

When a system in accordance with embodiments hereof is coupled to a syringe with a syringe loading guide attached to a syringe delivery ring, whereby a proximal segment of the syringe delivery ring is received within a coupling archway of the syringe loading guide with a distal-facing surface of the syringe loading guide in abutment with a bearing surface of a distal segment of the syringe delivery ring, a distance between a proximal-facing surface of the syringe loading guide and a proximal end of the syringe delivery ring corresponds to a small volume dose of a medication to be delivered from the syringe.

BRIEF DESCRIPTION OF DRAWINGS

The foregoing and other features and aspects of the present technology can be better understood from the following description of embodiments and as illustrated in the accompanying drawings. The accompanying drawings, which are incorporated herein and form a part of the specification, further serve to illustrate the principles of the present technology. The components in the drawings are not necessarily to scale.

DETAILED DESCRIPTION OF THE INVENTION

Specific embodiments of the present invention are now described with reference to the figures, wherein like reference numbers indicate identical or functionally similar elements. The terms "distal" and "proximal", when used in the following description to refer to a syringe or components of a loading and delivery system hereof are with respect to a position or direction relative to a treating clinician who is holding the syringe with the needle end pointed away from himself or herself. Thus, "distal" and "distally" refer to positions distant from or in a direction away from the treating clinician, and the terms "proximal" and "proximally" refer to positions near or in a direction toward the treating clinician.

The following detailed description is merely exemplary in nature and is not intended to limit the present technology or the application and uses of the present technology. Although the description of embodiments hereof is in the context of the accurate delivery of a small volume dose of a medication, particularly applicable to ocular surgeries and treatments, the present technology may also be used for other treatments at other locations or sites where it is deemed useful. Furthermore, there is no intention to be bound by any expressed or implied theory presented in the preceding technical field, background, brief summary or the following detailed description.

Figure 1:
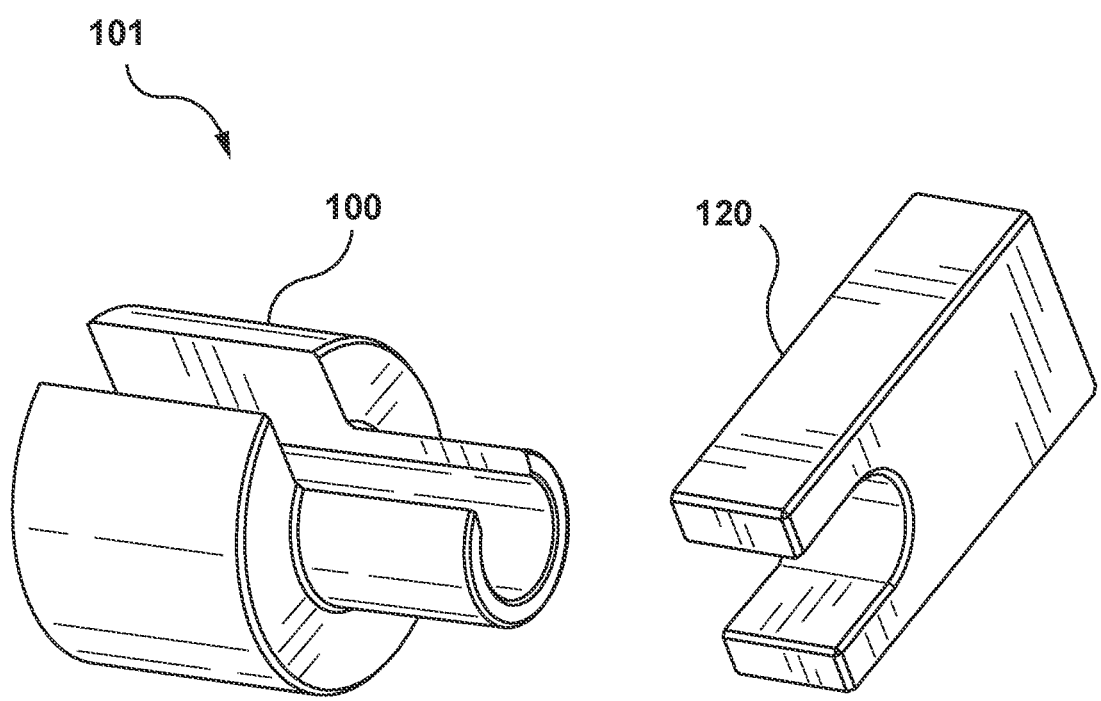
FIG. 1 depicts a perspective view illustration of a loading and delivery system for use with a syringe in accordance with an embodiment hereof.

Embodiments hereof are related to a kit for accurately loading a small volume dose of a medication within a syringe and for delivering the small volume dose of the medication at a treatment site. In accordance with embodiments hereof, a small volume dose as referred to herein may be a dose of medication of about 10 µl or less, a dose of medication of 7.5 µl or less and/or a dose of medication of 5 µl or less. The kit generally includes a loading and delivery system 101 in accordance herewith (shown in FIG. 1), a syringe, and a medication. The loading and delivery system 101 includes a syringe delivery ring 100 and a syringe loading guide 120, which may be used for example, to administer a small volume dose of a medication at the end of an ocular surgery. The syringe delivery ring 100 and the corresponding syringe loading guide 120 of the loading and delivery system 101 work together with a syringe to provide a precise volume of medication as prescribed by the treating clinician. It will be understood that the smaller a volume requirement of a dose, the more difficult or challenging accurate loading and delivery of the medication. Further, it will be understood that in applications utilizing very small volumes of a medication, even a slight variation in the delivered volume may have an undesirable or detrimental effect on the receiving patient. Stated another way, loading and delivery systems in accordance with the present invention are particularly useful in circumstances where precise volumes of medication or sample are required. For example, delivery of a precise volume can be important in applications in which: the delivery of an extremely potent drug product such that a small amount results in significant biological activity; a pharmaceutical may have side-effects if a non-precise volume is delivered; or where the site of administration is small, such as in the eye.

Figure 1A:
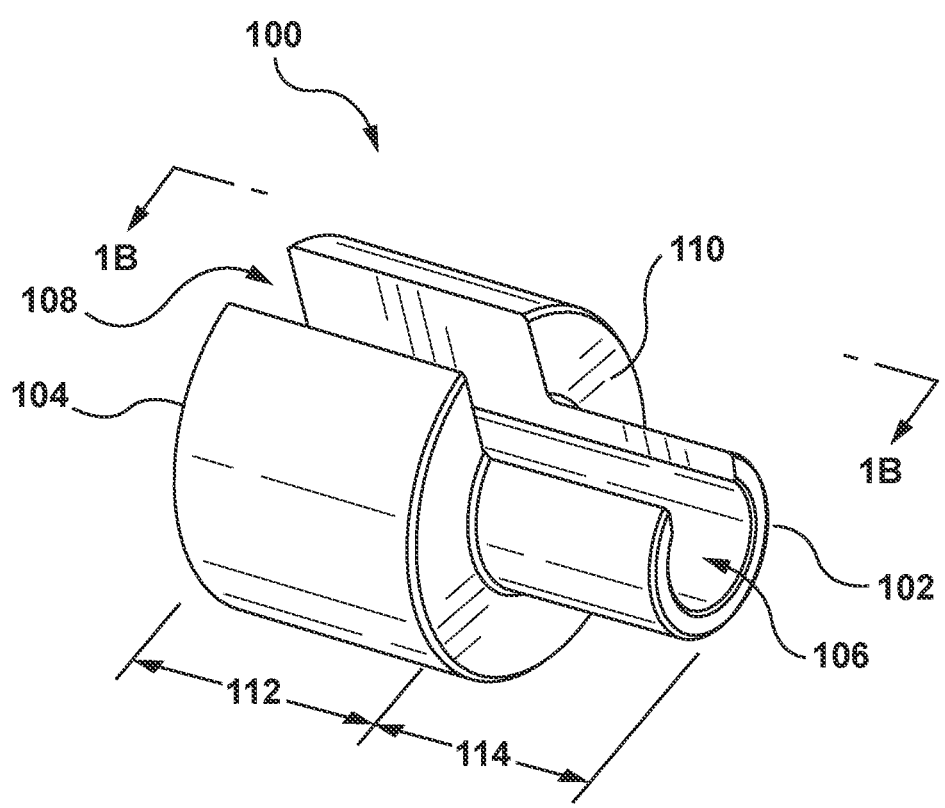
FIG. 1A depicts a perspective view illustration of a syringe delivery ring of the loading and delivery system of FIG. 1 in accordance with an embodiment hereof.
Figure 1B:
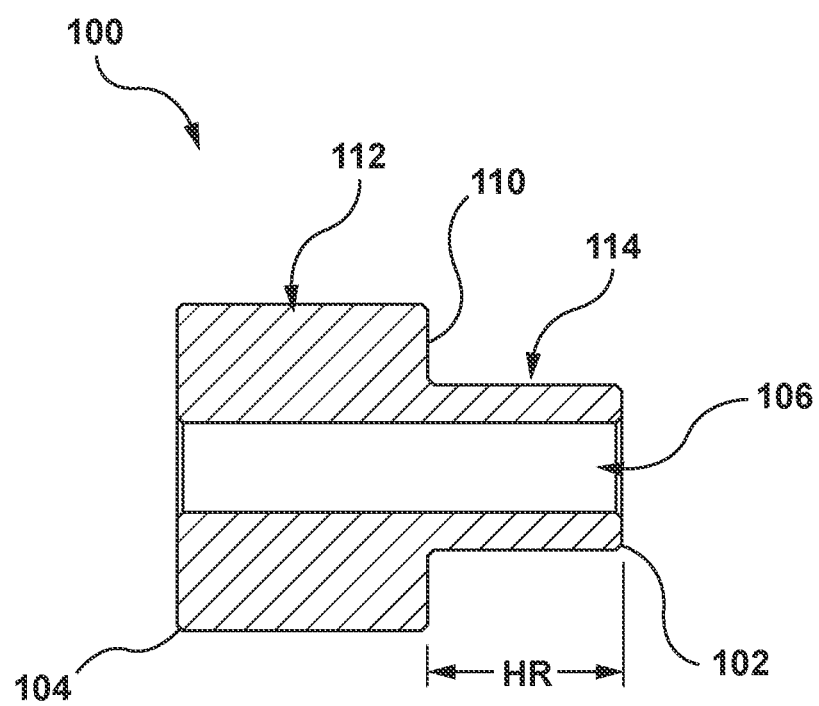
FIG. 1B depicts a sectional view of the syringe delivery ring of FIG. 1A taken along line B-B thereof.
Figure 1C:
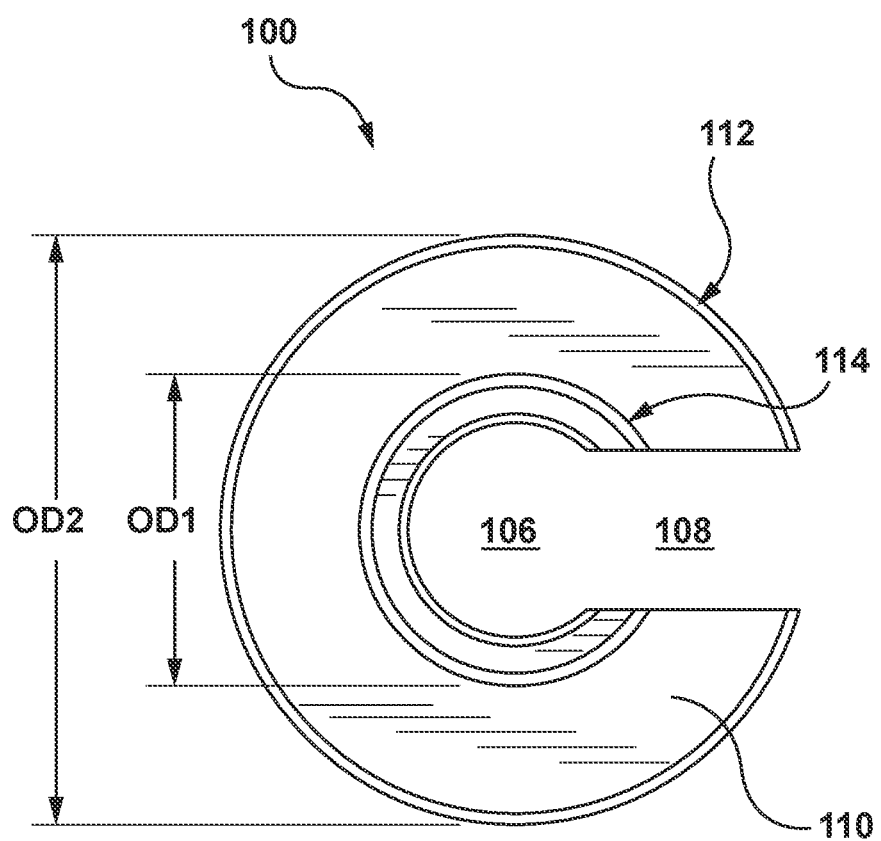
FIG. 1C depicts an end view illustration of the syringe delivery ring of FIG. 1A.

FIGS. 1A, 1B, and 1C are perspective, sectional side and end views, respectively, of a syringe delivery ring 100 in accordance with an embodiment hereof. When the syringe delivery ring 100 is disposed over a plunger rod of a syringe and abuts a barrel flange of a barrel of the syringe, the syringe delivery ring is configured to permit an accurate and precise dose of a medication as described below. The syringe delivery ring 100 includes a proximal end 102 and a distal end 104. A lumen 106 extends within the syringe delivery ring 100 from the proximal end 102 to the distal end 104. The lumen 106 is configured to slidably receive a plunger rod of a syringe therein as described below. In an embodiment, the lumen 106 has a constant diameter along its entire length. The syringe delivery ring 100 further includes a sidewall opening 108 that longitudinally extends from the proximal end 102 to the distal end 104 and that provides ingress and egress between an exterior of the syringe delivery ring 100 and the lumen 106. The sidewall opening 108 is configured to receive a plunger rod of a syringe there through such that the plunger rod may be slidably received within the lumen 106 to couple the syringe delivery ring 100 to the plunger rod of the syringe. The syringe delivery ring 100 has a stepped exterior profile, similar to a tiered wedding cake, with an outer diameter OD1 of a proximal segment 114 being smaller than an outer diameter OD2 of a distal segment 112 and having a proximal-facing bearing surface 110 defined there between. The bearing surface 110 is a planar, annular surface generally transverse to the lumen 106. As used herein, the term "generally transverse" means within manufacturing tolerances. The proximal segment 114 has a height HR, as best shown in FIG. 1B.

Figure 2A:
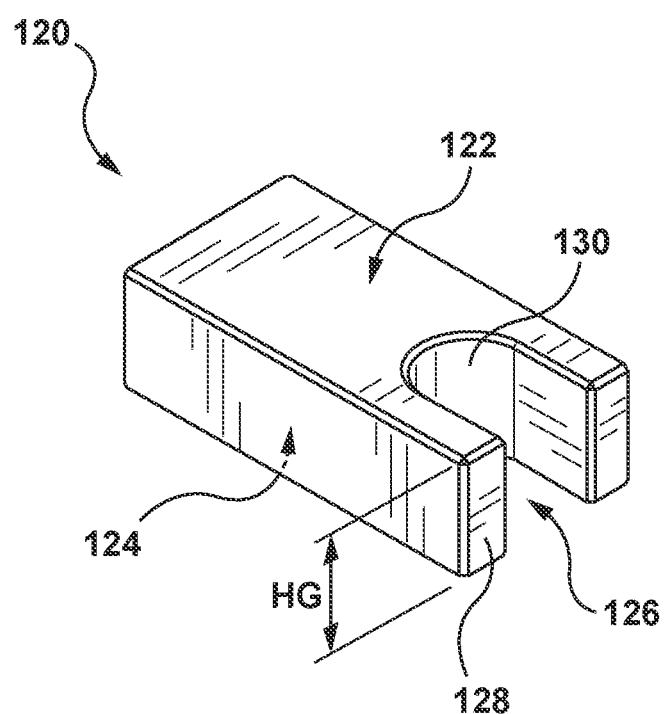
FIG. 2A depicts a perspective view illustration of a syringe loading guide of the loading and delivery system of FIG. 1 in accordance with an embodiment hereof.
Figure 2B:
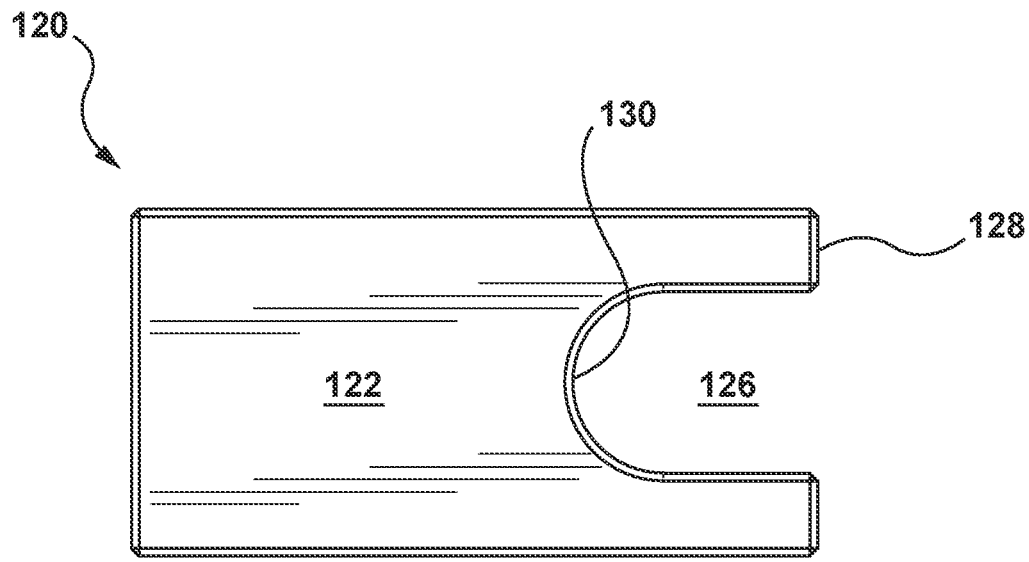
FIG. 2B depicts a top view illustration of the syringe loading guide of FIG. 2A.
Figure 2C:
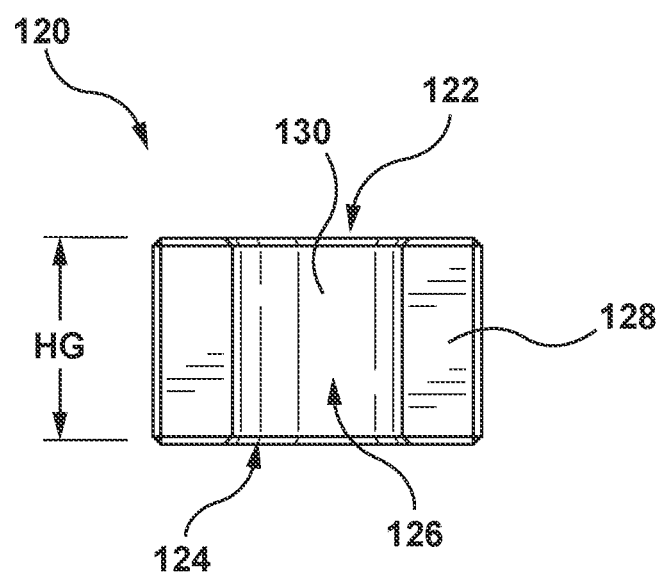
FIG. 2C depicts an end view illustration of the syringe loading guide of FIG. 2A.

FIGS. 2A, 2B, and 2C are perspective, top and end views, respectively, of a syringe loading guide 120 in accordance with an embodiment hereof. The syringe loading guide 120 is configured to be utilized with the corresponding syringe delivery ring 100 to permit the accurate and precise loading of a desired small volume dose of a medication as described below. The syringe loading guide 120 is a rectangular parallelepiped having a proximal-facing surface 122 and a distal-facing surface 124. The syringe loading guide 120 further includes a coupling archway 126, or arch-like shaped recess, within an end 128 of the syringe loading guide 120. In an embodiment, the coupling archway 126 may be described as defining an inner radius 130 that corresponds to an outer circumference or profile of the proximal segment 114 of the syringe loading guide 100. The coupling archway 126 extends between the proximal-facing surface 122 and the distal-facing surface 124 on the syringe loading guide 120. The coupling archway 126 is configured to receive the proximal segment 114 of the syringe delivery ring 100, as described below. A height HG of the syringe loading guide 120 is greater than the height HR of the proximal segment 114 of the corresponding syringe delivery ring 100. When a loading and delivery system of the syringe delivery ring 100 and the syringe loading guide 120 are coupled to a syringe with the syringe loading guide 120 attached to the syringe delivery ring 100, whereby the proximal segment 114 of the syringe delivery ring 100 is received within the coupling archway 126 of the syringe loading guide 120 with the distal-facing surface 124 of the syringe loading guide 120 in abutment with the bearing surface 110 of the distal segment 112 of the syringe delivery ring 100, a distance D1 (shown in FIG. 5) between the proximal-facing surface 122 of the syringe loading guide 120 and the proximal end 102 of the syringe delivery ring 100 corresponds to a small volume dose of a medication to be delivered from the syringe, as explained in more detail below. Stated another way and with reference to FIGS. 5, 16A and 16B, a difference between a first height HG of the syringe loading guide 120 and a second height HR of the proximal segment 114 of the syringe delivery ring 100 corresponds to a distance D2 that a plunger seal travels within a barrel of a syringe to deliver a small volume dose of a medication disposed therein, wherein D1 is equal to D2 as explained in more detail below.

When the syringe delivery ring 100 is disposed over a plunger rod of a syringe and abuts a barrel flange of a barrel of the syringe, and the proximal segment 114 of the syringe delivery ring 100 is received in the coupling archway 126 of the syringe loading guide 120 such that the distal-facing surface 124 of the syringe loading guide 120 abuts the bearing surface 110 of the syringe delivery ring 100, the combination of the syringe delivery ring 100 and the corresponding syringe loading guide 120 is configured to provide a stable platform for accurate loading of a small volume of a medication into the corresponding syringe, as described below. The syringe delivery ring 100 and the syringe loading guide 120 may each be formed of materials such as, but not limited to polymers, for instance ULTEM 1000, DUPONT DELRIN acetal resin, etc. Further, the syringe delivery ring 100 and the syringe loading guide 120 may each be formed by methods, non-limiting examples of which include molding, machining, milling casting, or any other suitable method.

Figure 3:
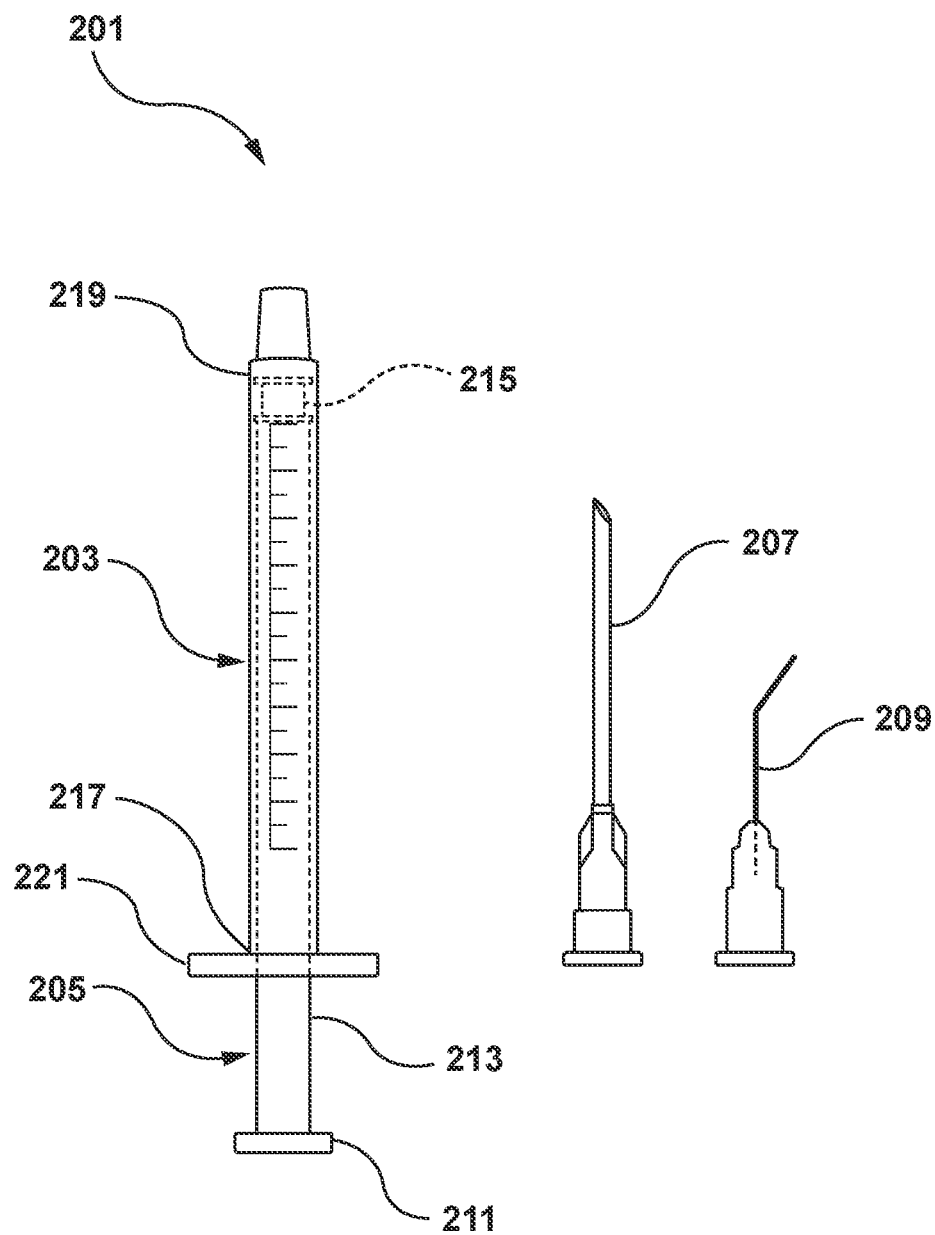
FIG. 3 depicts a syringe suitable for use with embodiments hereof.

FIG. 3 illustrates a syringe 201 for use with a loading and delivery system of a syringe delivery ring 100 and a corresponding syringe loading guide 120 in accordance with an embodiment hereof. The syringe includes a barrel 203, a plunger 205, a syringe needle 207, and an optional syringe cannula 209. The plunger 205 includes a plunger flange 211 at a proximal end of a plunger rod 213 and a plunger seal 215 at a distal end of the plunger rod 213. A barrel flange 221 is disposed at a proximal end 217 of the barrel 203. A distal end 219 of the barrel 203 is configured to releasably receive the syringe needle 207 or the syringe cannula 209 thereon. Although the syringe needle 209 is shown having a bent shaft in FIG. 3 and other figures hereof, this is shown by way of example and not limitation, as the syringe needle 209 may have a straight shaft and be used to load and administer a dose of a medication so as to eliminate any need for the syringe cannula 209 or another syringe needle.

Figure 4:
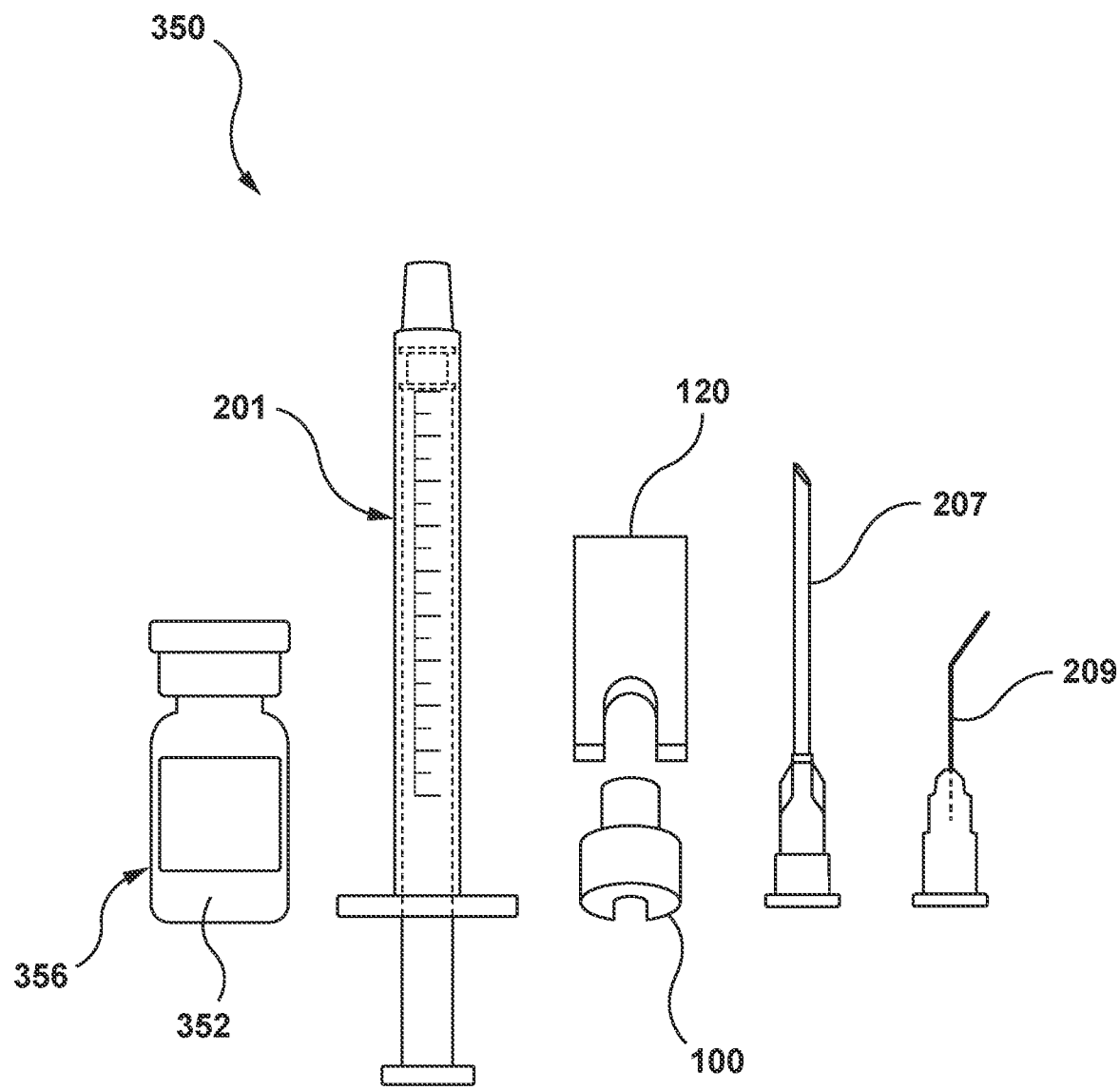
FIG. 4 depicts components of a kit for loading and delivering a medication with a syringe in accordance with an embodiment hereof.

FIG. 4 illustrates a kit 350 for accurately loading and delivering a small volume dose of a medication with a syringe in accordance with an embodiment hereof. The kit 350 includes a set of corresponding components including a loading and delivery system, such as a syringe delivery ring 100 and a syringe loading guide 120, a syringe 201 (including a syringe needle 207 and an optional syringe cannula 209), and a medication 352 generally retained within a vial 356. The medication 352 may be any medication or drug product suitable for use with the syringe 201.

In an embodiment, a kit 350 of the present invention may include one or more containers, such as the vial 356, including a medication or a drug product. In other embodiments, a kit 350 of the present invention may including a medication or a drug product pre-loaded into a syringe of the kit.

Non-limiting examples of a medication or a drug product for use in embodiments described herein may contain one or more pharmaceutically active ingredients. Such ingredients include bevacizumab, ranibizumab, infliximab, indomethacin, nepafenac, pegaptanib sodium, choline fenofibrate, bevasiranib, rapamycin, minocycline, mecamylamine, ketorolac tromethamine, denufosol tetrasodium, hydrocortisone, betamethasone, beclomethasone, beclomethasone dipropionate, budesonide, clobetasol, cortisol, cortisone, dexamethasone, fludrocortisone, flunisolide, flunisolide hemihydrate, fluocinolone, fluocinolone acetonide, fluocinonide, fluticasone, fluticasone propionate, methylprednisolone, mometasone, mometasone furoate anhydrous, mometasone furoate monohydrate, prednisone, prednisolone, triamcinolone, and triamcinolone acetonide, and tyrosine kinase inhibitors, such as afatinib, alectinib, apatinib, axitinib, bafetinib, baricitinib, binimetinib, bosutinib, brigatinib, cabozantinib, canertinib, cediranib, CEP-37440, ceritinib, cobimetinib, crenolanib, crizotinib, CYT387, damnacanthal, dasatinib, doramapimod, entrectinib, erlotinib, filgotinib, foretinib, fostamatinib, grandinin, gefitinib, ibrutinib, icotinib, imatinib, JSI-124, lapatinib, lestaurtinib, lenvatinib, linifanib, masitinib, motesanib, mubritinib, neratinib, nilotinib, nintedanib, pacritinib, pazopanib, pegaptanib, PF-06463922, ponatinib, quizartinib, radotinib, regorafenib, ruxolitinib, selumetinib, semaxanib, sorafenib, staurosporine, sunitinib, SU6656, TG101348, tivozanib, toceranib, tofacitinib, trametinib, TSR-011, vandetanib, vatalanib, vemurafenib, and X-396. These pharmaceutical active ingredients may be dissolved, suspended, or otherwise mixed with inactive ingredients such as water or other pharmaceutically acceptable excipients.

In one embodiment, the medication comprises dexamethasone suspended in acetyl triethyl citrate. For example, the medication may be in a vial 356 comprising 0.5 mL of 9% w/w dexamethasone suspended in acetyl triethyl citrate. In another embodiment a volume of 5 μl of 9% w/w dexamethasone (equivalent to 517 micrograms) suspended in acetyl triethyl citrate medication is delivered from a syringe 201 using the loading and delivery system.

Figure 5:
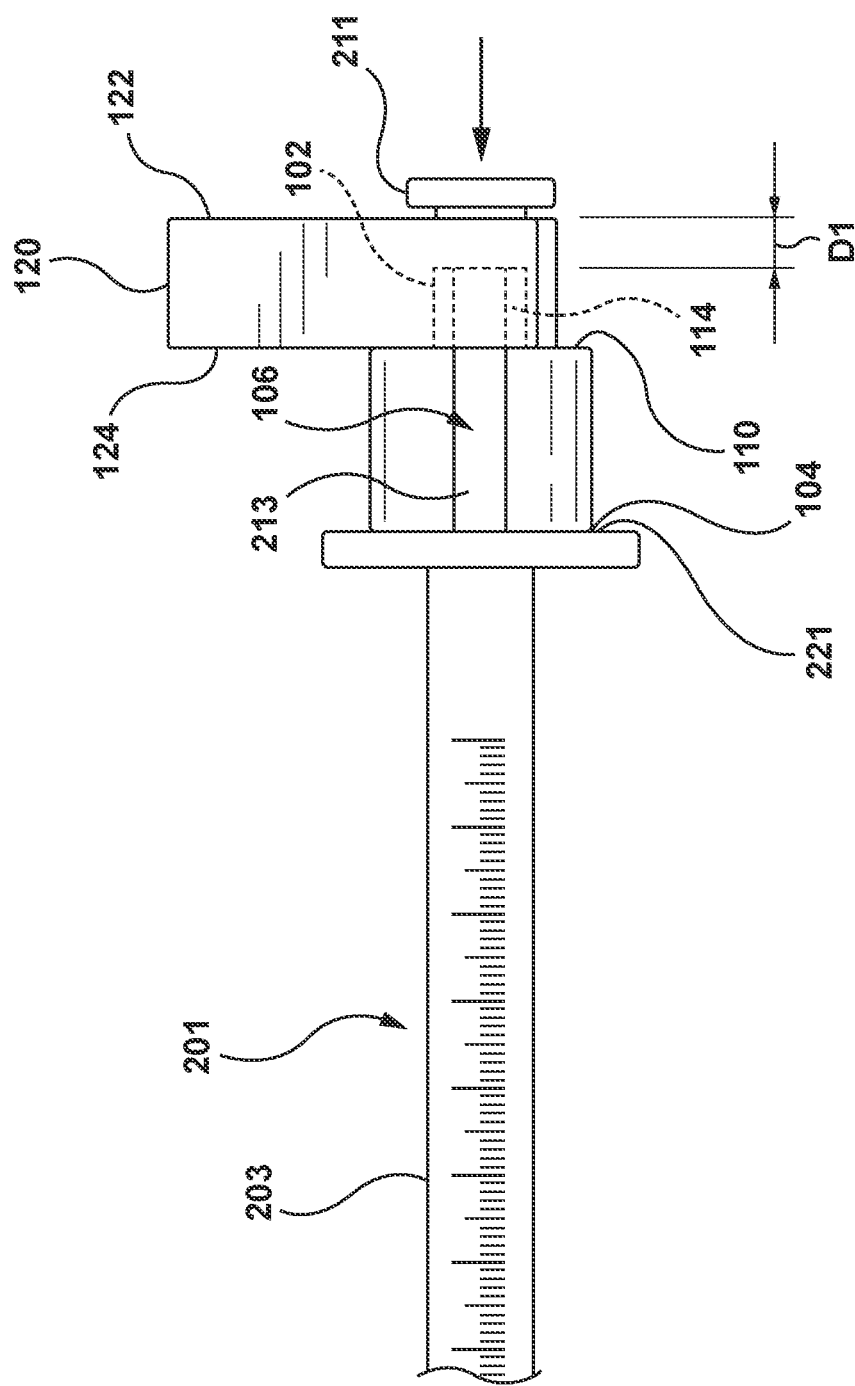
FIG. 5 depicts the loading and delivery system of FIG. 1 attached to a syringe in a loaded configuration.

A loading and delivery system in accordance herewith, configured for use with a corresponding syringe, includes a loaded configuration that occurs when a small volume dose has been defined/loaded and is ready for administration and a delivered configuration that occurs after the small volume dose has been administered. The loaded configuration is shown in FIG. 5, with a plunger rod 213 of a syringe 201 slidably received within a lumen 106 of a syringe delivery ring 100 and a distal end 104 of the syringe delivery ring 100 abutting a barrel flange 221 of the syringe 201. As well in the loaded configuration, the proximal segment 114 of the syringe delivery ring 100 is received within the coupling archway 126 of the syringe loading guide 120 and the distal-facing surface 124 of the syringe loading guide 120 abuts the bearing surface 110 of the syringe delivery ring 100. In addition in the loaded configuration, a plunger flange 211 of the syringe 201 abuts a proximal-facing surface 122 of the syringe loading guide 120, and a distance D1 between the proximal-facing surface 122 of the syringe loading guide 120 and a proximal end 102 of the syringe delivery ring 100 defines a small volume dose of a medication (not visible in FIG. 5) disposed within the barrel 203 of the syringe 201. The bearing surface 110 of the syringe delivery ring 100 is configured to stabilize the syringe loading guide 120 when the system is in the loaded configuration. More specifically, the bearing surface 110 of the syringe delivery ring 100 provides a stable platform on which the syringe loading guide 120 rests, thus providing increased stability to the syringe loading guide 120, which in turn provides increased accuracy in loading a small volume dose of a medication in accordance herewith.

Figure 6:
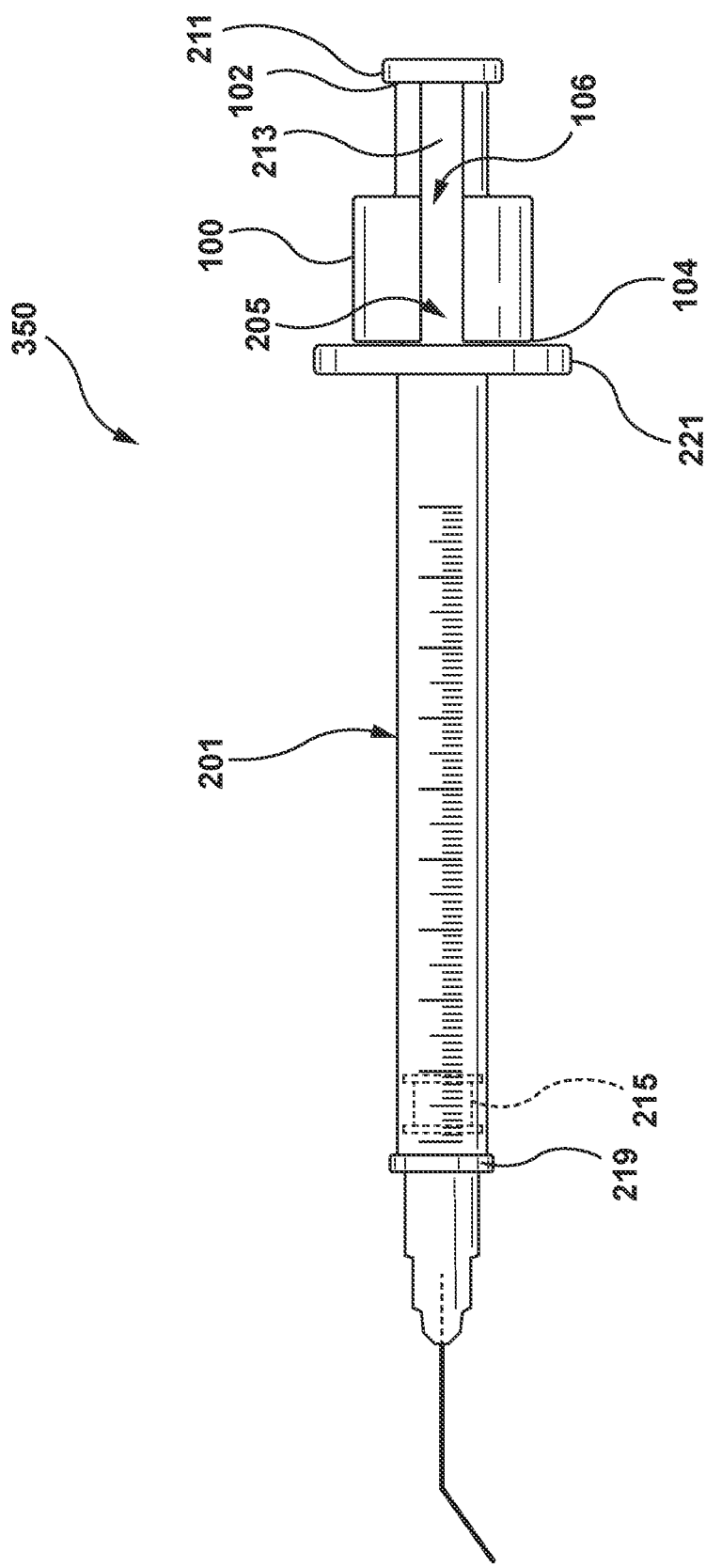
FIG. 6 depicts the loading and delivery system of FIG. 1 attached to a syringe in a delivered configuration.

FIG. 6 shows a loading and delivery system in accordance herewith in a delivered configuration, with the plunger rod 213 slidably received within the lumen 106 of the syringe delivery ring 100 and a distal end 104 of the syringe delivery ring 100 abutting the barrel flange 221 of the syringe 201. As well, the plunger flange 211 of the syringe 201 is shown abutting the proximal end 102 of the syringe delivery ring 100 after delivery of the small volume dose of the medication. When the system is in the delivered configuration, the syringe delivery ring 100 provides a hard stop to any further advancement of the plunger flange 211 of the plunger rod 213 and is configured to prevent the plunger seal 215 from contacting a distal end 219 of the barrel 203 of the syringe 201, thereby preventing any unintended delivery of medication beyond the desired small volume dose. It should be readily understood by the description herein that when the system transitions from the loaded configuration of FIG. 5 to the delivered configuration of FIG. 6, a distance traveled by the plunger 205 corresponds to a desired small volume dose of medication to be delivered from the syringe 201.

Figure 7:
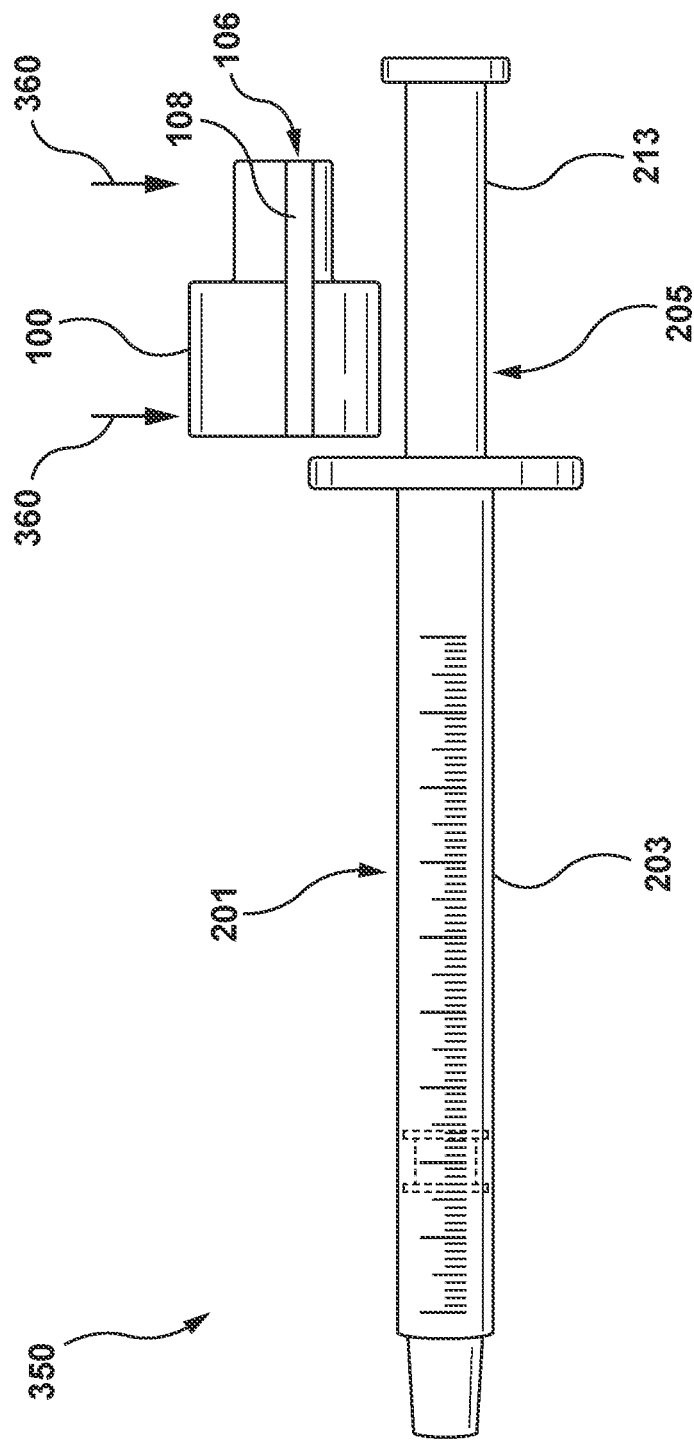
FIG. 7 depicts a step in a method of using the loading and delivery system of FIG. 1, wherein the syringe delivery ring is positioned adjacent to a plunger rod of a syringe.
Figure 8:
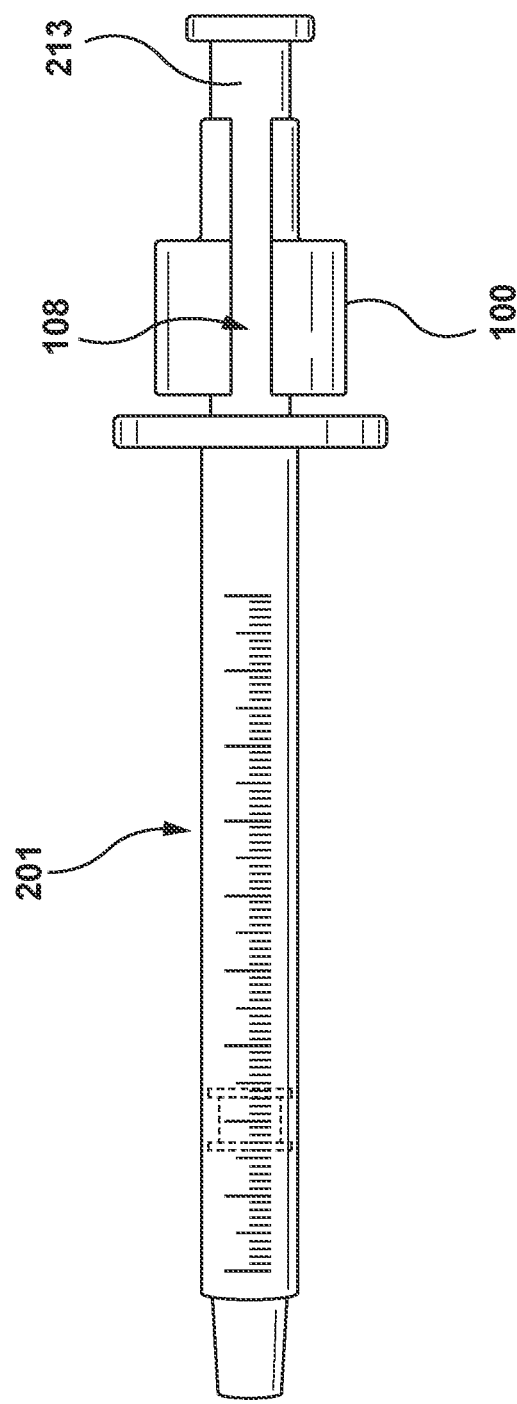
FIG. 8 depicts a step in the method of using the loading and delivery system of FIG. 1, wherein the syringe delivery ring is coupled to the plunger rod of the syringe.

With an understanding of a system for loading and delivering a small volume dose of medication and the components of a kit 350 in accordance herewith, FIGS. 7-15 illustrate the interaction of the various components with reference to a method of accurately loading a small volume dose of a medication into a syringe and delivering the small volume dose of the medication at a desired treatment site. Following the opening of the kit 350 and removal of its components from respective pouches or protective films, a plunger 205 is withdrawn from a barrel 203 of a syringe 201 approximately one (1) inch, as shown in FIG. 7. A syringe delivery ring 100 is then positioned adjacent to the exposed portion of the plunger 205, or more precisely the exposed plunger rod 213, with the sidewall opening 108 facing the exposed plunger rod 213. A force or pressure is applied to the syringe delivery ring 100 in a direction of arrows 360 such that the exposed plunger rod 213 of the plunger 205 passes through or traverses the sidewall opening 108, by spreading apart the walls that define the sidewall opening 108, and enters the lumen 106 of the syringe delivery ring 100. Due to the resilient nature of the syringe delivery ring 100, once the plunger rod 213 of the plunger 205 has passed through the sidewall opening 108, the sidewall opening 108 returns to an initial shape such that the syringe delivery ring 100 is slidably coupled to the plunger rod 213 of the syringe 201, as shown in FIG. 8.

Figure 9:
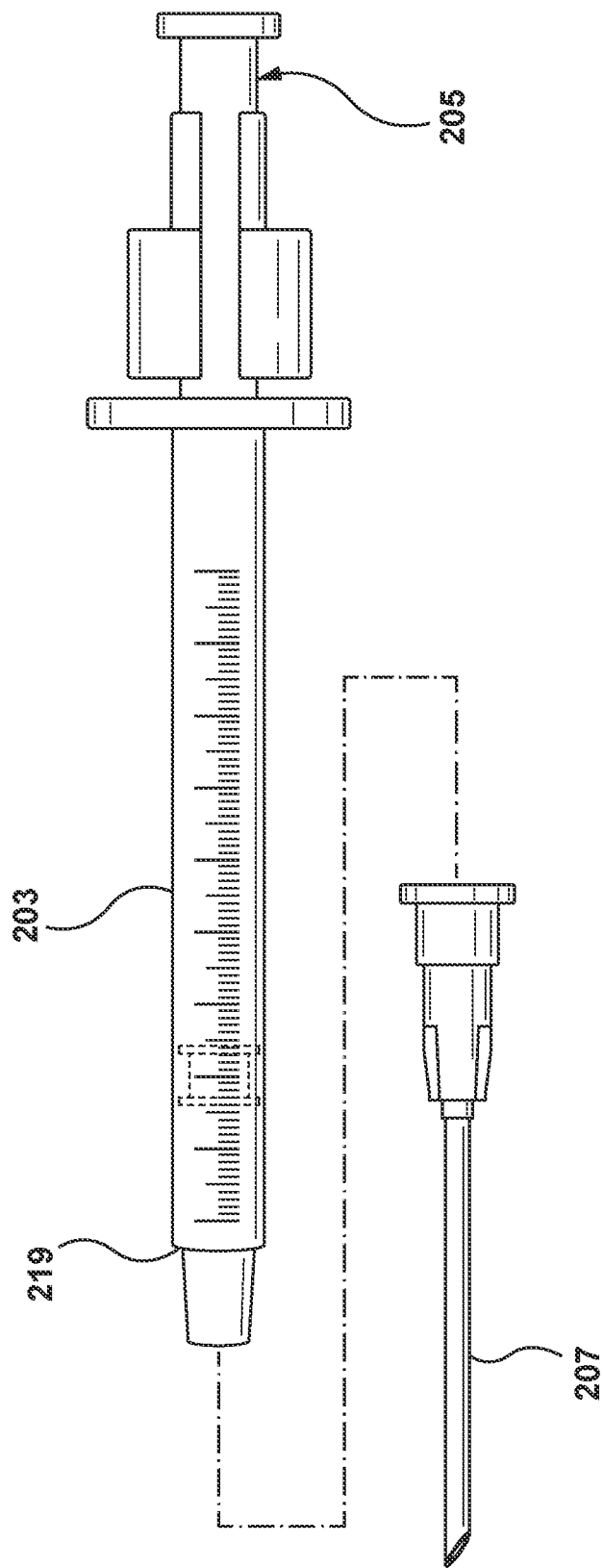
FIG. 9 depicts a step in the method of using the loading and delivery system of FIG. 1, wherein a syringe needle is releasably coupled to a distal end of the syringe.

In a next step, a syringe needle 207 is releasably coupled to a distal end 219 of the barrel 203 of the syringe 201, as shown in FIG. 9. The plunger 205 is depressed completely, then withdrawn to fill the barrel 203 with air.

A medication 352 is then prepared for loading into the syringe 201. Preparation of the medication 352 for loading may include but is not limited to agitating a vial 356 containing the medication 352 for a specific duration of time.

Figure 10:
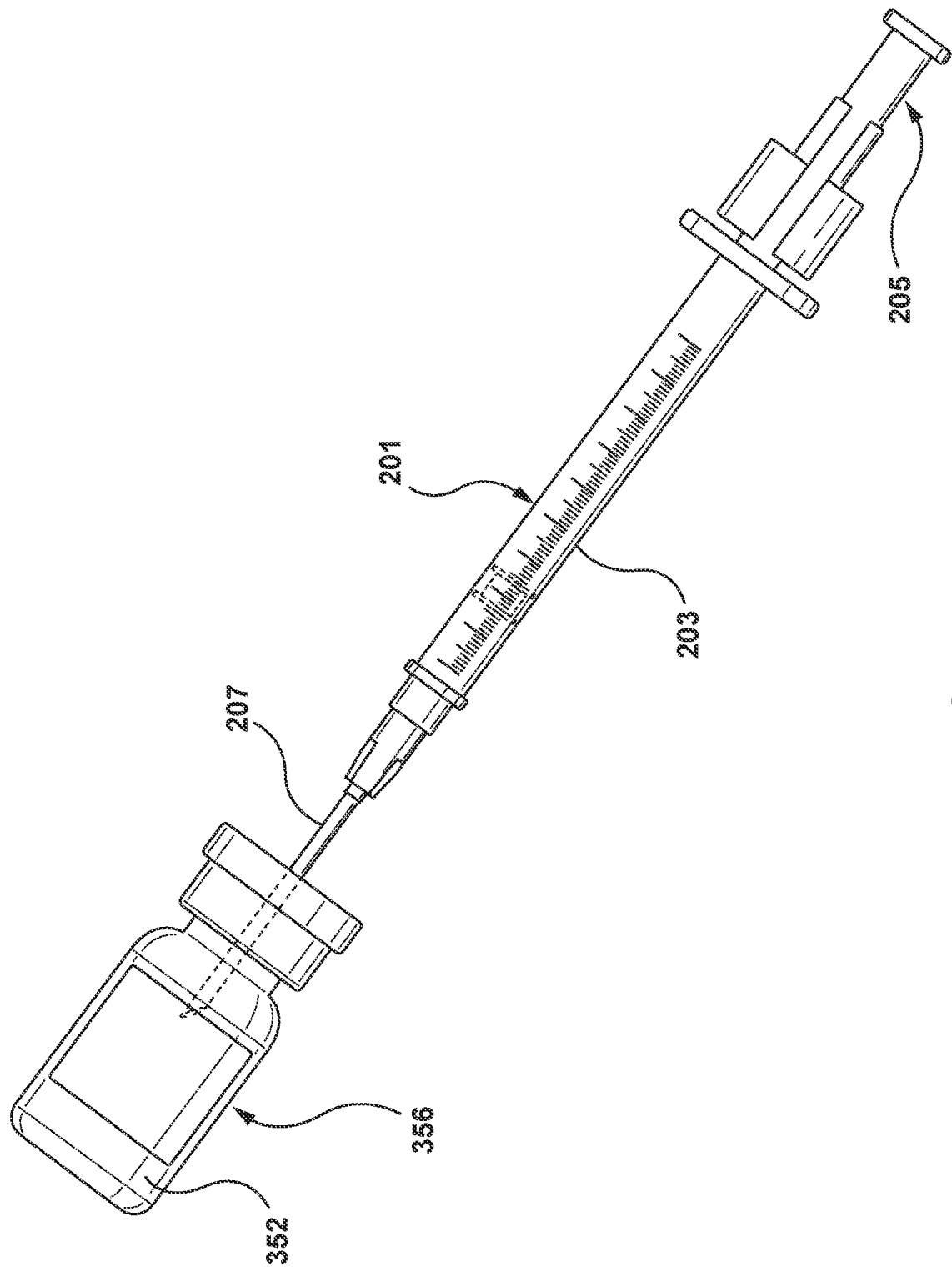
FIG. 10 depicts a step in the method of using the loading and delivery system of FIG. 1, wherein a medication is drawn into a barrel of the syringe
Figures 11A, 11B:
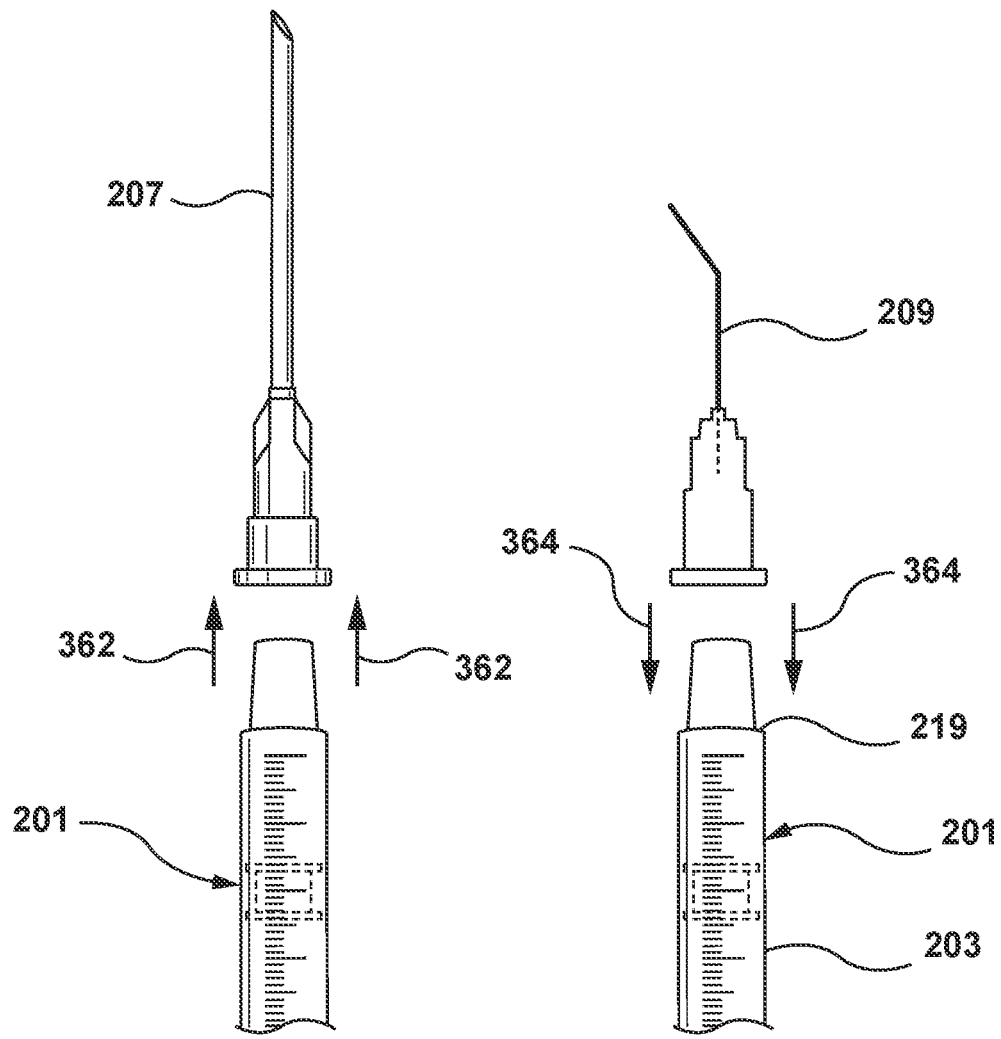
FIGS. 11A and 11B depict a step in the method of using the loading and delivery system of FIG. 1, wherein the syringe needle of the syringe is exchanged for a syringe cannula.
Figure 12:
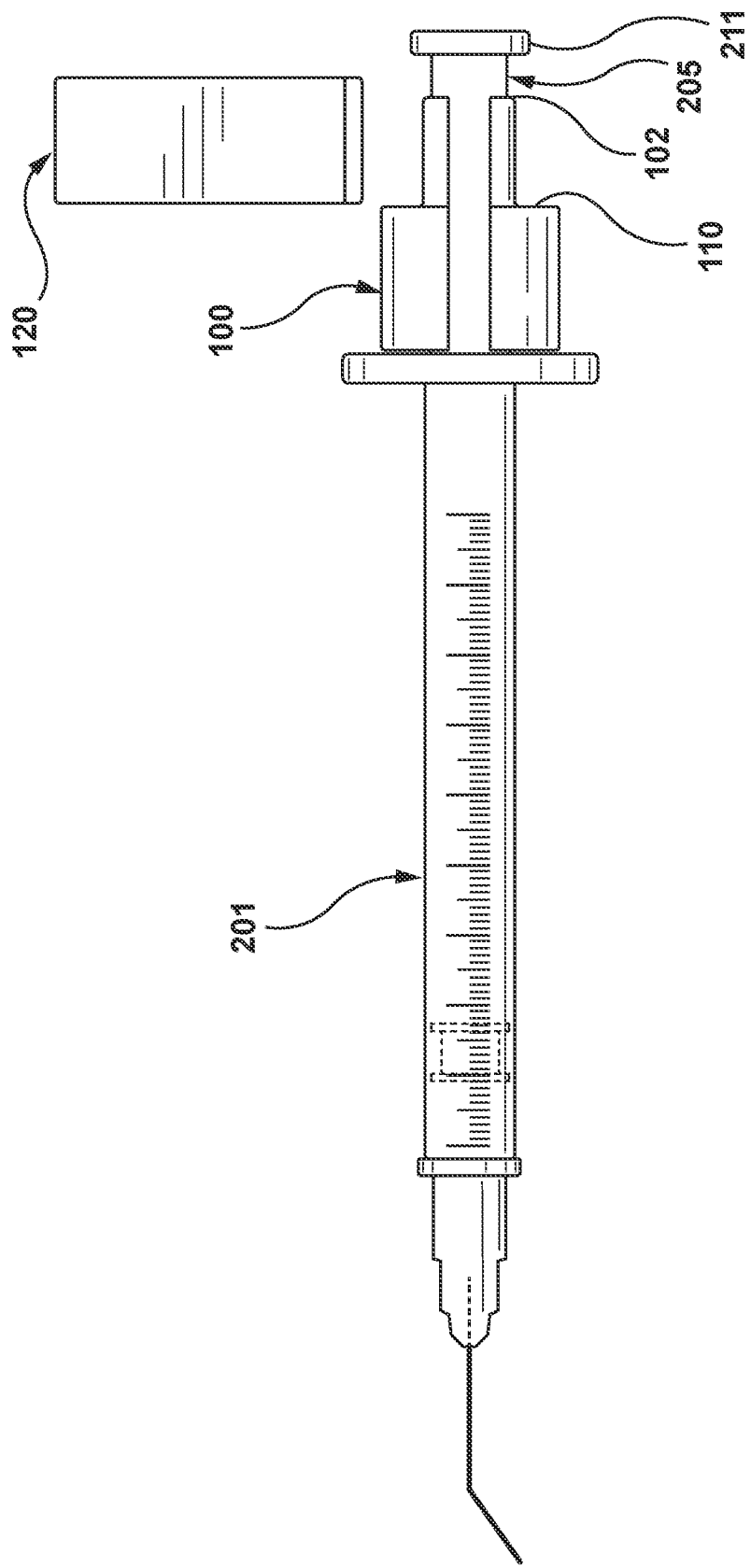
FIG. 12 depicts a step in the method of using the loading and delivery system of FIG. 1, wherein a plunger of the syringe is depressed to expel air from the barrel of the syringe.

When the medication 352 is ready for loading into the syringe 201, the vial 356 is inverted, the syringe needle 207 is inserted into the vial 356, and the plunger 205 is depressed to expel the air contained in the barrel 203 into the vial 356. When the air has been expelled, the plunger 205 is proximally retracted to draw the medication 352 into the barrel 203 of the syringe 201, as shown in FIG. 10. For example, and not by way of limitation, the plunger 205 is retracted to draw approximately 0.01 mL to 0.5 mL, preferably about 0.02 mL, of medication 352 into the syringe barrel 203.

After a suitable volume of the medication 352 is drawn into the syringe barrel 203, the syringe needle 207 is removed from the vial 356. In an optional embodiment, the syringe needle 207 may also be exchanged or replaced with a syringe cannula 209 by removing the syringe needle 207, as indicated by the arrows 362 in FIG. 11A, and attaching the syringe cannula 209 to the distal end 219 of the syringe barrel 203, as indicated by the arrows 364 in FIG. 11B. In an alternate embodiment, the syringe needle 207 may be replaced with a different gauge needle.

The syringe 201 is then held vertically and the plunger 205 (not visible in FIG. 11B) is depressed to expel the air from the syringe 201. As best viewed in FIG. 12, it will be noted that the plunger 205 is depressed just enough to expel the air from the syringe barrel 203, but not so much that the plunger flange 211 abuts the proximal end 102 of the syringe delivery ring 100. More precisely, sufficient space must be left between the bearing surface 110 of the coupled syringe delivery ring 100 and the plunger flange 211 to position the syringe loading guide 120 there between.

Figure 13:
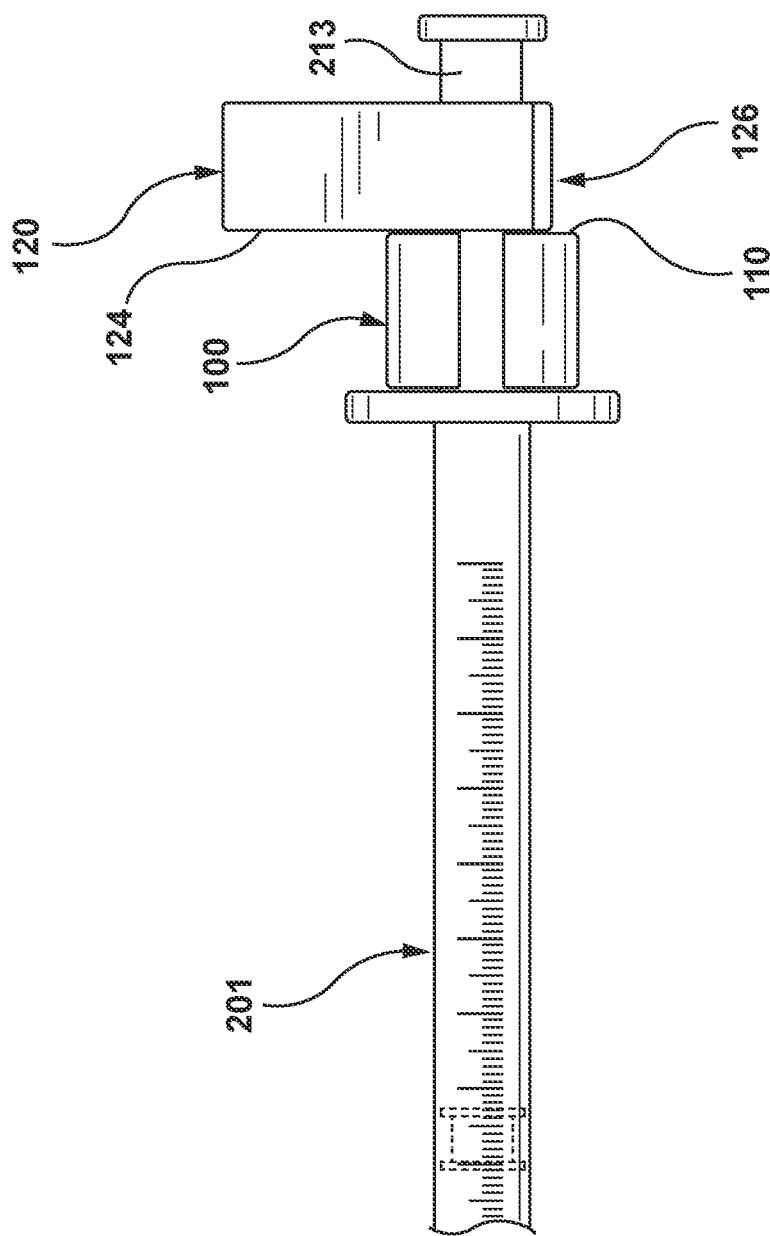
FIG. 13 depicts a step in the method of using the loading and delivery system of FIG. 1, wherein the syringe loading guide is in abutment with a bearing surface of the syringe delivery ring and positioned over a proximal portion of the syringe delivery ring to extend proximal thereof.

As shown in FIG. 13, with the air expelled from the syringe 201, the syringe loading guide 120 is attached to the proximal segment 114 (not visible in FIG. 13) of the syringe delivery ring 100 such that the proximal segment 114 is received within the coupling archway 126 of the syringe loading guide 120. More precisely, the syringe loading guide 120 is positioned such that the proximal segment 114 (not visible in FIG. 13) of the syringe delivery ring 100 abuts the inner radius 130 (not visible in FIG. 13) of the coupling archway 126, and the distal-facing surface 124 of the syringe loading guide 120 abuts the bearing surface 110 of the syringe delivery ring 100. The syringe loading guide 120 resting or abutting the bearing surface 110 of the syringe delivery ring 100 provides increased stability to the syringe loading guide 120 as previously explained.

Figure 14:
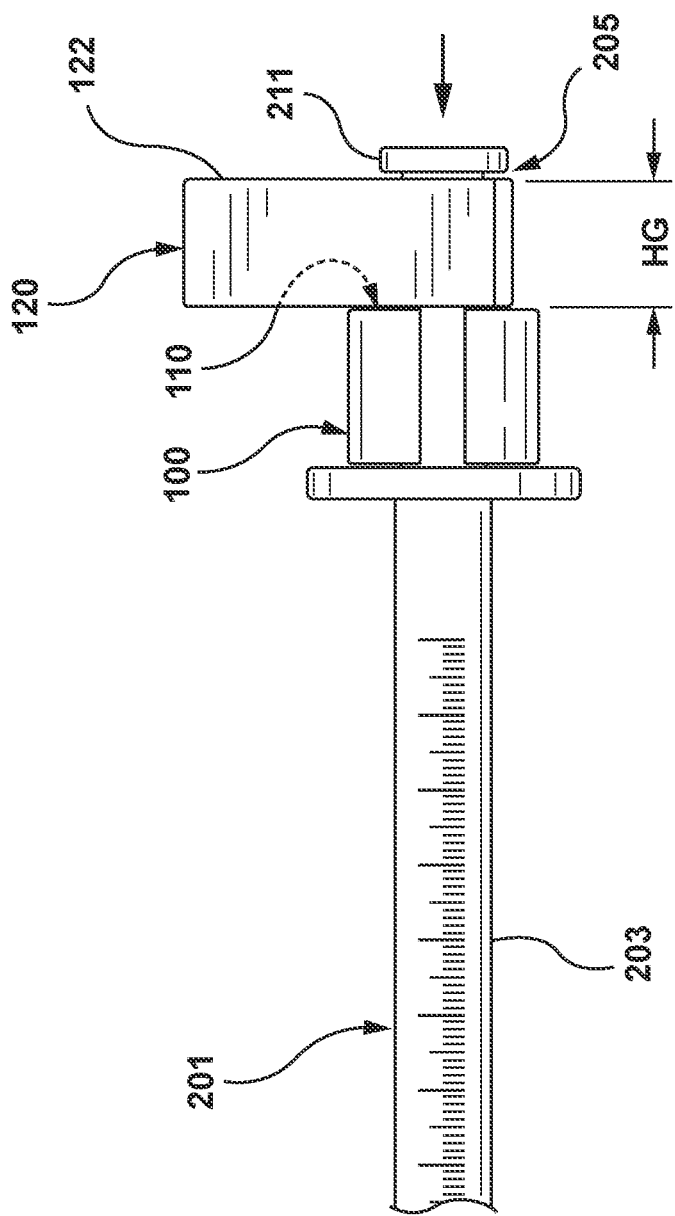
FIG. 14 depicts a step in the method of using the loading and delivery system of FIG. 1, wherein a plunger flange of the plunger is depressed and in abutment with a proximal-facing surface of the syringe loading guide.

FIG. 14 shows a next step in the method wherein the plunger 205 is depressed to expelling an excess of medication 352 (not visible in FIG. 14) therefrom. More specifically, the plunger 205 is depressed until the plunger flange 211 abuts or contacts the proximal-facing surface 122 of the syringe loading guide 120. This loads a precise small volume dose of the medication in the barrel 203 of the syringe 201. It will be understood that a difference between a first height HG of the syringe loading guide 120 and a second height HR of the proximal segment 114 of the syringe delivery ring 100 corresponds to a distance the plunger seal 215 travels within the barrel 203 of the syringe 201 to deliver a small volume dose of the medication. The stabilized loading platform formed by the syringe loading guide 120 resting on the bearing surface 110 of the syringe delivery ring 100 insures a precise and extremely accurate small volume dose of medication 352 (not visible in FIG. 14) is disposed within the barrel 203 of the syringe 201.

Figure 15:
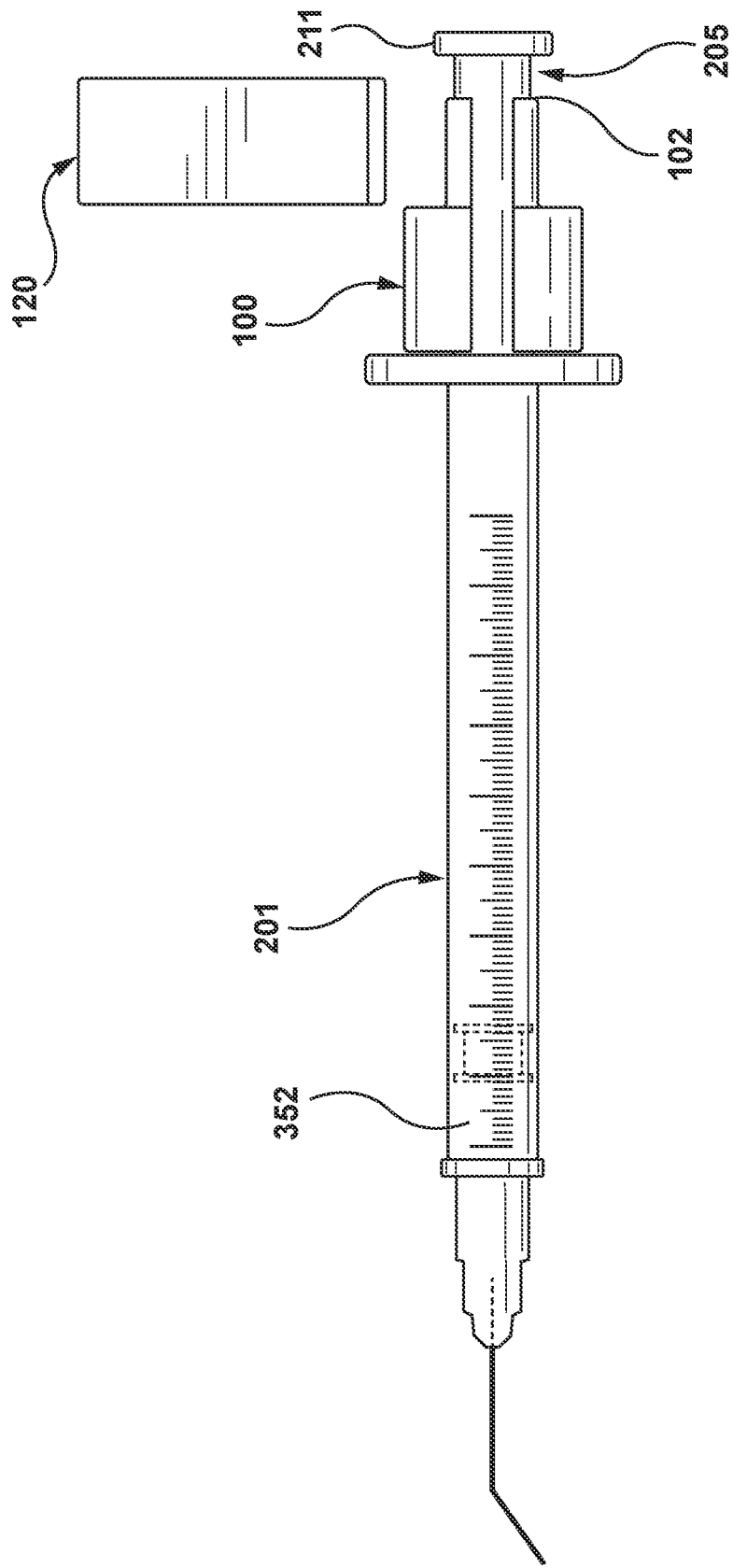
FIG. 15 depicts a step in the method of using the loading and delivery system of FIG. 1, wherein the syringe loading guide is removed from the syringe delivery ring and the plunger rod of the syringe.

In a next step shown in FIG. 15, after loading of the small volume dose of medication 352 within the syringe 201, the syringe loading guide 120 is removed from the syringe delivery ring 100 and the plunger 205. When the syringe loading guide 120 has been removed, the syringe 201 with the syringe delivery ring 100 coupled thereto are ready for delivery of the medication 352 to the desired treatment site. Delivery of the medication 352 from the syringe 201 is accomplished by depressing the plunger 205 until the plunger flange 211 abuts or contacts and is stopped by the proximal end 102 of the syringe delivery ring 100.

Figure 16A:
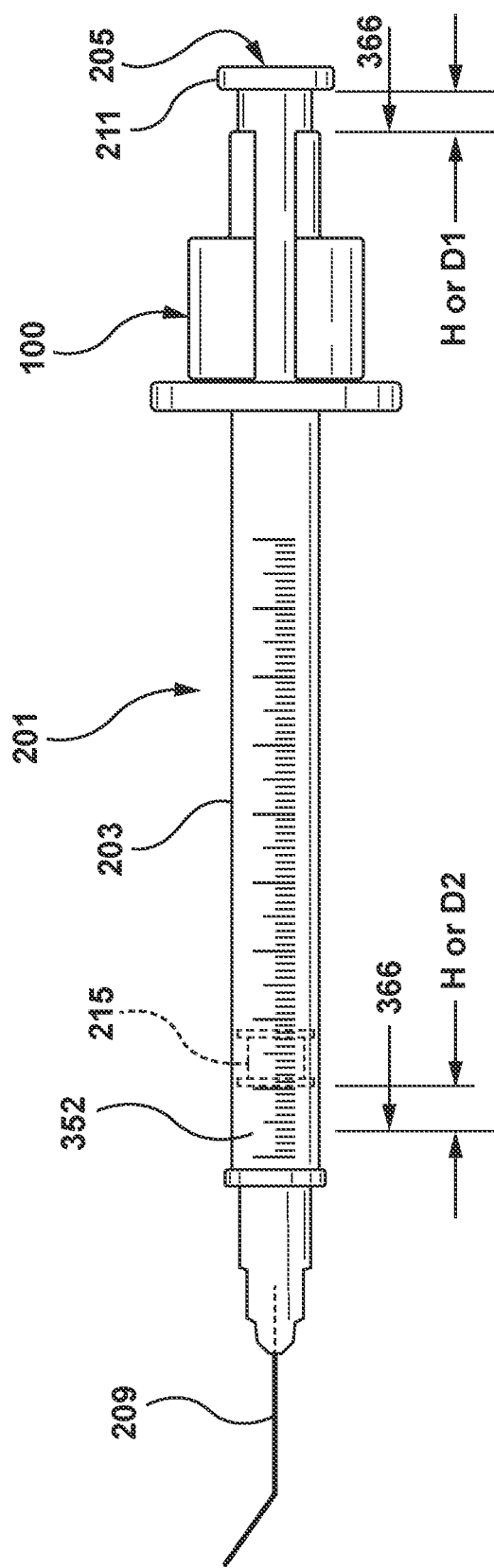
FIG. 16A depicts the syringe of FIG. 15, wherein the syringe is in the loaded configuration, with the syringe loading guide removed.
Figure 16B:
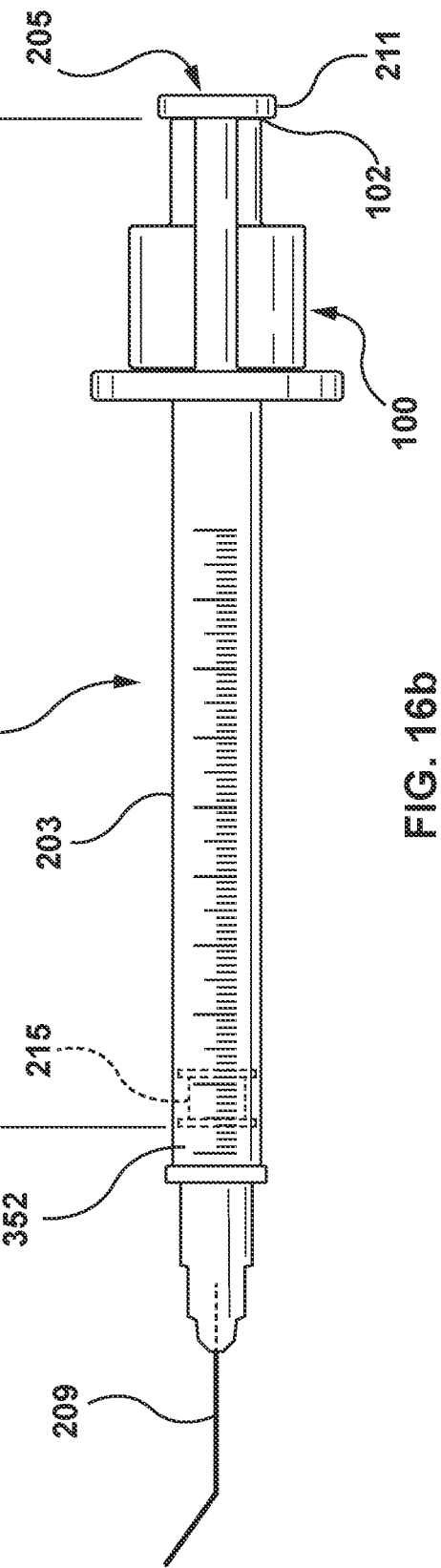
FIG. 16B depicts the syringe of FIG. 15, wherein the syringe is in the delivered configuration.

With reference to FIGS. 16A and 16B, a distance H or D1/D2 that the plunger 205 travels as the medication 352 is delivered corresponds to the desired small volume dose of the medication 352 delivered. In accordance with embodiment of the present invention, the distance H or D1/D2 is determined as described below. FIGS. 16A and 16B illustrate the movement of the plunger 205 relative to the barrel 203 as the desired small volume dose of the medication is delivered from the syringe 201. The arrows 366 illustrates the movement of the plunger 205 when depressed by a user to deliver the desired small volume dose of the medication 352 from the syringe 201. More precisely, the plunger 205 moves the height or distance H (D1/D2) as the kit transitions from the configuration of FIG. 16A (which is the loaded configuration with the syringe loading guide 120 removed) to the delivered configuration of FIG. 16B. The plunger 205 is depressed until the plunger flange 211 contacts the proximal end 102 of the syringe delivery ring 100. Stated another way, the plunger 205 is depressed the height or distance H (D1) until stopped by the syringe delivery ring 100. The plunger seal 215 of the plunger 205 moves an equivalent height or distance H (D2) within the barrel 203. When the plunger seal 215 moves the height H, the precise desired small volume dose of the medication 352 is delivered from the syringe. It is important to note that due to the hard stop provided by the syringe delivery ring, the plunger seal 215 of the plunger 205 never bottoms out or makes contact within the barrel 203. This insures that the plunger seal 205 during delivery does not inadvertently push out more medication than intended due to varying levels of force provided by various users of the syringe. If the plunger seal 215 were allowed to bottom out within the barrel 203, pressure applied on the plunger 205 by the user during delivery can deform the plunger seal 215. Any deformation of the plunger seal 215 during delivery will change the volume of medication 352 that is delivered. More specifically, deformation of the plunger seal 215 during the delivery will increase a volume of medication 352 that is delivered. When dealing with small volume doses of delivered medication, a small increase of delivered medication can lead to serious complications. Thus, the combination of the syringe delivery ring 100 and the corresponding syringe loading guide 120 (not visible in FIGS. 16A and 16B) with the corresponding syringe 201 provides a precise and accurate desired small volume dose of delivered medication 352.

A height H (shown in FIGS. 16A and 16B) that a plunger moves within a barrel of a syringe to be used with a loading and delivery system in accordance herewith, during medication delivery, is based upon a desired small volume dose of a medication to be delivered and an inner radius of the syringe barrel. An equation that expresses this relationship is:

$$V = \pi r^2 H$$

In the equation, V is the desired small volume dose, r is an inner radius of the syringe barrel, and H is a height or distance (D1/D2) the syringe plunger needs to longitudinally translate within the syringe barrel for delivering the desired small volume dose V. Therefore, knowing a respective syringe to be used and a desired small volume dose of medication to be delivered, the height H may be calculated, as shown below.

$$H = V/\pi r^2$$

The height H, as shown in FIGS. 16A and 16B is a distance the syringe plunger moves and can be expressed as the difference between the height HG (FIG. 2A) of the syringe loading guide 120 and the height HR (FIG. 1A) of the proximal segment 114 of the syringe delivery ring 100. This can be expressed as:

$$H = HG - HR$$

The height H is known from the previous calculation and the height HR of the proximal segment 114 of the syringe delivery ring 100 is known. Thus, a height HG of a syringe loading guide 120 can be calculated for any desired small volume dose of medication to be delivered for the corresponding syringe and the corresponding syringe delivery ring 100. The height HG can be found by using the following equation:

$$HG = H + HR$$

TABLE 2

Composition of IBI-10090 Administration Syringe Kit Assembly

| Sterile Pouch | Component | Manufacturer/Supplier[a] | Manufacturer/Supplier Part Number |
|---|---|---|---|
| IBI-10090 Syringe Assembly | Syringe Ring Natural ULTEM 1000 HU USP Class VI | Marx Digital Machining (MDM)-custom made | CT-sr-002 |
| | Syringe Guide Natural ULTEM 1000 HU USP Class VI | Marx Digital Machining (MDM)-custom made | CT-sg-006 |
| Syringe | Terumo Syringe Tuberculin Without Needle (Single Use) | Terumo Pharmaceutical Solutions | SS-01T |
| Syringe Cannula | Anterior Chamber Cannula 25 Gauge × 8 mm Bend | MSI Precision Specialty Instrument | CA2350 |
| Syringe Needle | Terumo K-Pack II Needle 18 G × 1½" SB (Single Use) | Terumo Pharmaceutical Solutions | KN-1838SB |

[a]Commercially available except where noted

Thus, the relationship between a syringe 201, a syringe delivery ring 100, and a syringe loading guide 120 are critical in loading and delivering a precise desired volume or dose of a medication at a desired treatment site. Stated another way, for a known syringe 201 with a known inner radius r of the barrel 203 and the corresponding syringe delivery ring 100 with the known proximal segment 114 height HR, the desired small volume dose of medication 352 to be delivered is determined by selection of an appropriate syringe loading guide 120 with a height HG corresponding to the desired small volume dose. Thus, for a known syringe 201 and a known corresponding syringe delivery ring 100, a variation in the height HG of the corresponding syringe loading guide 120 will vary the desired dose of a medication.

While various embodiments have been described above, it should be understood that they have been presented only as illustrations and examples of the present technology, and not by way of limitation. It will be apparent to persons skilled in the relevant art that various changes in form and detail may be made therein without departing from the spirit and scope of the present technology. Thus, the breadth and scope of the present technology should not be limited by any of the above-described embodiments, but should be defined only in accordance with the appended claims and their equivalents. It will also be understood that each feature of each embodiment discussed herein, and of each reference cited herein, may be used in combination with the features of any other embodiment. All patents and publications discussed herein are incorporated by reference herein in their entirety.

What is claimed is:

1. A kit for accurately loading a small volume dose of medication within a syringe and for delivering the small volume dose of medication at a treatment site, the kit comprising:
    a syringe including a plunger and a barrel for holding a medication, the plunger including a plunger rod, a plunger flange at a proximal end of the plunger rod and a plunger seal at a distal end of the plunger rod, wherein the barrel is sized to receive a length of the plunger rod and the plunger seal therein;
    a syringe delivery ring including a lumen and a sidewall opening that extend from a proximal end to a distal end thereof, the sidewall opening being configured to permit the plunger rod of the syringe to be slidably received within the lumen of the syringe delivery ring, and the syringe delivery ring further including a proximal segment and a distal segment, wherein the proximal segment has a smaller outer diameter than the distal segment;
    a syringe loading guide including a proximal-facing surface, a distal-facing surface, and a coupling archway configured to attach to the proximal segment of the syringe delivery ring during loading, wherein a first height of the syringe loading guide is greater than a second height of the proximal segment of the syringe delivery ring; and
    a medication for loading within and for delivery by the syringe, wherein a difference between the first height of the syringe loading guide and the second height of the proximal segment of the syringe delivery ring corresponds to a distance the plunger seal travels within the barrel of the syringe to deliver a small volume dose of the medication.

2. The kit of claim 1, wherein when the syringe loading guide is disposed on the syringe delivery ring during loading, with the plunger flange in abutment with the proximal-facing surface of the syringe loading guide, the difference between the first height of the syringe loading guide and the second height of the proximal segment of the syringe delivery ring also corresponds to a distance defined between the proximal end of the syringe delivery ring and the plunger flange.

3. The kit of claim 1, wherein a proximal-facing bearing surface of the distal segment of the syringe delivery ring is configured to stabilize the syringe loading guide during loading of the medication.

4. The kit of claim 3, wherein the proximal-facing surface of the syringe loading guide is configured to abut with the plunger flange of the syringe during loading, and the distal-facing surface of the syringe loading guide is configured to abut with the proximal-facing bearing surface of the distal segment of the syringe delivery ring during loading.

5. The kit of claim 1, further comprising a syringe needle.

6. The kit of claim 1, further comprising a syringe cannula.

7. The kit of claim 1, wherein the medication is contained in one of a vial and the barrel of the syringe.

8. The kit of claim 7, wherein the medication comprises dexamethasone suspended in acetyl triethyl citrate.

9. The kit of claim 8, wherein the medication is contained within the vial and comprises 0.5 mL of 9% w/w dexamethasone suspended in acetyl triethyl citrate.

10. The kit of claim 8, wherein the medication comprises 9% w/w dexamethasone suspended in acetyl triethyl citrate.

11. The kit of claim 1, wherein the small volume dose of the medication to be delivered comprises 5 μl of 9% w/w dexamethasone (equivalent to 517 micrograms) suspended in acetyl triethyl citrate.

12. A loading and delivery system for use with a syringe to accurately load a small volume dose of medication within the syringe and to deliver the small volume dose from the syringe at a treatment site, the system comprising:

a syringe delivery ring including a lumen and a sidewall opening that extend from a proximal end to a distal end thereof, the sidewall opening being configured to permit a plunger rod of the syringe to be slidably received within the lumen of the syringe delivery ring, and the syringe delivery ring further including a proximal segment and a distal segment, wherein the proximal segment has a smaller outer diameter than the distal segment; and a syringe loading guide including a proximal-facing surface, a distal-facing surface, and a coupling archway that is configured to attach to the proximal segment of the syringe delivery ring during loading, wherein a first height of the syringe loading guide is greater than a second height of the proximal segment of the syringe delivery ring, and wherein when the system is coupled to the syringe, with the syringe loading guide attached to the syringe delivery ring whereby the proximal segment of the syringe delivery ring is received within the coupling archway of the syringe loading guide, a distance between the proximal-facing surface of the syringe loading guide and the proximal end of the syringe delivery ring corresponds to the small volume dose of medication to be delivered from the syringe.

13. The system of claim 12, wherein when the system is coupled to the syringe in a dose loaded configuration, the plunger rod of the syringe is slidably received within the lumen of the syringe delivery ring with the distal end of the syringe delivery ring in abutment with a barrel flange of the syringe, and the proximal segment of the syringe delivery ring is received within the coupling archway of the syringe loading guide with the distal-facing surface of the syringe loading guide in abutment with a proximal-facing bearing surface of the distal segment of the syringe delivery ring, such that the distance between the proximal-facing surface of the syringe loading guide and the proximal end of the syringe delivery ring, which is the distance between a plunger flange of the syringe and the proximal end of the syringe delivery ring, corresponds to a distance a plunger seal of the syringe will travel within a barrel of the syringe to deliver the small volume dose of medication.

14. The system of claim 13, wherein when the system is coupled to the syringe in a dose delivered configuration, after removal of the syringe loading guide and delivery of the small volume dose from the syringe at the treatment site, the distal end of the syringe delivery ring remains in abutment with the barrel flange of the syringe, the plunger flange of the syringe is in abutment with the proximal end of the syringe delivery ring, and the syringe delivery ring is configured to prevent the plunger seal from contacting a distal end of the barrel of the syringe, wherein the distance traveled by the plunger seal as the system transitions from the dose loaded configuration to the dose delivered configuration corresponds to the small volume dose of medication delivered from the syringe.

* * * * *